US009612145B2

(12) United States Patent
Hurmuzlu et al.

(10) Patent No.: US 9,612,145 B2
(45) Date of Patent: Apr. 4, 2017

(54) REVOLVING ULTRASOUND FIELD MULTIPHASE FLOWMETER

(71) Applicants: Yildirim Hurmuzlu, McKinney, TX (US); Edmond Richer, Richardson, TX (US)

(72) Inventors: Yildirim Hurmuzlu, McKinney, TX (US); Edmond Richer, Richardson, TX (US)

(73) Assignees: Yildirim Hurmuzlu, McKinney, TX (US); Edmond Richer, Richardson, TX (US)

( * ) Notice: Subject to any disclaimer, the term of this patent is extended or adjusted under 35 U.S.C. 154(b) by 0 days.

(21) Appl. No.: 14/862,753

(22) Filed: Sep. 23, 2015

(65) Prior Publication Data

US 2016/0341586 A1      Nov. 24, 2016

Related U.S. Application Data

(60) Provisional application No. 62/164,940, filed on May 21, 2015.

(51) Int. Cl.
*G01F 1/66* (2006.01)
*G01F 1/74* (2006.01)
(Continued)

(52) U.S. Cl.
CPC .................. *G01F 1/74* (2013.01); *G01F 1/44* (2013.01); *G01F 1/66* (2013.01); *G01F 1/68* (2013.01)

(58) Field of Classification Search
CPC ..................................... G01F 1/74; G01F 1/66
(Continued)

(56) References Cited

U.S. PATENT DOCUMENTS 4,162,630 A    7/1979   Johnson
4,532,812 A *  8/1985   Birchak ................. E21B 21/08
                                                 73/152.21

(Continued)

FOREIGN PATENT DOCUMENTS

WO      201000138595 A1    12/2010
WO      201400165833 A2    10/2014

OTHER PUBLICATIONS

International Search Report and Written Opinion of Korean Intellectual Property Office dated Aug. 16, 2016, 15 pp.

*Primary Examiner* — Jewel V Thompson
(74) *Attorney, Agent, or Firm* — Edwin S. Flores; Chalker Flores, LLP

(57) ABSTRACT

The present invention includes a device and method for determining the flow of one or more phases of a multiphase fluid mixture comprising: a tube, a pipe, a main body or any combinations thereof comprising an interior and an exterior, wherein the interior receives a multiphase fluid mixture for the determination of the fractions in the multiphase; a first ultrasound field detector ring comprising: two or more pairs of transversal paired dual frequency ultrasound transmitter/receivers are on the same normal plane and are positioned in a transversal direction to a flow of the multiphase fluid mixture on the exterior of the tube, pipe, or main body, wherein the sampled volume covers a part of or the whole cross-section of the flow volume; and a computer connected to the ultrasound transmitter/receivers that determines the one or more phases of a multiphase fluid mixture.

37 Claims, 5 Drawing Sheets

(51) Int. Cl.
*G01F 1/44* (2006.01)
*G01F 1/68* (2006.01)

(58) Field of Classification Search
USPC .......................... 73/861.04, 861.26, 861.27
See application file for complete search history.

(56) References Cited

U.S. PATENT DOCUMENTS

| | | | | |
|---|---|---|---|---|
| 4,726,235 | A * | 2/1988 | Leffert | G01F 1/66 |
| | | | | 73/861.04 |
| 5,600,073 | A * | 2/1997 | Hill | G01B 5/28 |
| | | | | 73/30.03 |
| 5,719,329 | A * | 2/1998 | Jepson | G01F 1/24 |
| | | | | 73/597 |
| 6,047,602 | A * | 4/2000 | Lynnworth | G01F 1/662 |
| | | | | 73/632 |
| 6,049,602 | A * | 4/2000 | Foladare | H04M 3/5125 |
| | | | | 370/352 |
| 2010/0274503 | A1 | 10/2010 | Hurmuzlu et al. | |
| 2014/0136126 | A1* | 5/2014 | Ao | G01N 9/00 |
| | | | | 702/48 |

* cited by examiner

REVOLVING ULTRASOUND FIELD MULTIPHASE FLOWMETER

CROSS-REFERENCE TO RELATED APPLICATIONS

This application claims priority to U.S. Provisional Application Ser. No. 62/164,940 filed May 21, 2015, the entire contents of which are incorporated herein by reference.

TECHNICAL FIELD OF THE INVENTION

The present invention relates in general to the field of flowmeters, and more particularly, to a revolving ultrasound field multiphase flowmeter.

STATEMENT OF FEDERALLY FUNDED RESEARCH

None.

BACKGROUND OF THE INVENTION

Without limiting the scope of the invention, its background is described in connection with ultrasound meters.

Multiphase meters have attracted the attention of the oil production industry because of their accuracy and cost savings as opposed to analyzing discrete samples of multiphase fluid to determine fractions of oil, water, and gas. Development of accurate and compact multiphase metering devices that can be installed at well heads in remote onshore fields and unmanned offshore platforms continues to be a technological challenge. Data acquired by such devices may be used in reservoir management and production allocation inasmuch as the particular volumetric fractions of oil, water, and gas can be determined. Therefore this data is highly valuable. However, conventional devices have had difficulty in producing an accurate measurement of various properties of the monitored multiphase while withstanding the harsh environments in which such devices are typically installed.

Multiple array ultrasound devices that may acquire real-time spatial data from volumetric specimens have been developed for medical applications. Advanced data and signal processing systems and display technologies have been developed for aerospace and the defense industries. These technologies are unsuitable to quantify phase fractions and flow rates of oil, gas, and water in a multiphase flow stream in an oil pipeline. In particular, the field conditions of the oil production environment are extremely harsh because of high pressure and temperatures, and because of abrasive particles such as sand. Furthermore, the presence of gas bubbles in the flow streams as well as effects due to high temperature and pressure in the pipeline require specialized models to obtain accurate data collection and analysis.

SUMMARY OF THE INVENTION

In one embodiment, the present invention includes a device for determining the flow of one or more phases of a multiphase fluid mixture comprising: a tube, a pipe, a main body or any combinations thereof comprising an interior and an exterior, wherein the interior receives a multiphase fluid mixture for the determination of the fractions in the multiphase; a first ultrasound field detector ring comprising: two or more pairs of transversal paired single or multiple frequency ultrasound transmitter/receivers are on the same normal plane and are positioned in a transversal direction to a flow of the multiphase fluid mixture on the exterior of the tube, pipe, or main body, wherein the sampled volume covers a part of or the whole cross-section of the flow volume; and a computer connected to the ultrasound transmitter/receivers that determines the one or more phases of a multiphase fluid mixture. In one aspect, the device further comprises one or more ultrasound field detector rings adjacent to the first ultrasound field detector ring, each of the one or more ultrasound field detectors positioned in a transversal direction to a flow of the multiphase fluid mixture. In another aspect, the device further comprises one or more ultrasound field detector rings adjacent to the first ultrasound field detector ring are placed on one or more parallel planes. In another aspect, the device further comprises a pressure sensor to sense a fluid pressure of the multiphase fluid mixture, a temperature sensor to sense a fluid temperature of the multiphase fluid mixture, a total mass flow meter for a real-time determination of the multiphase fluid mixture, and a computer to determine a gas fraction, a water fraction, and a non-water fluid fraction of the multiphase fluid mixture, based on the sensed fluid pressure, the sensed fluid temperature, and at least one characteristic of the detected ultrasonic wave in the multiphase fluid. In another aspect, the ultrasound transmitter/receivers are in contact with the multiphase fluid. In another aspect, the ultrasound transmitter/receivers are capable of at least one of: scanning at the same time, scanning in series, scanning in parallel, scanning in pulses, or scanning with one pair acting as a transmitter and the second pair acting as a receiver.

In another aspect, a Gas-Volumetric-Fraction (GVF) is estimated using a moving average of an amplitude of all signal(s) received by the ultrasound transmitter/receivers in a scan configuration after ultrasound propagation through the multiphase fluid mixture. In another aspect, a GVF is estimated using at least one characteristic of one or more of a signal(s) received for a scan configuration after propagation through the mixture at the ultrasound transmitter/receivers. In another aspect, the ultrasound transmitter/receivers are capable of detecting one or more ultrasonic flashes that are transient in time and have at least one of a larger amplitude or a different frequency spectra from that transmitted. In another aspect, the ultrasound transmitter/receivers are capable of detecting one or more ultrasonic flashes that are transient in time and have at least one of a larger amplitude or different frequency spectra from that transmitted, wherein the ultrasound flashes are calculated using a Fourier transform of the signal (spectral analysis). In another aspect, the ultrasound transmitter/receivers are capable of detecting one or more ultrasonic flashes, wherein the detection threshold for flashes can be constant or can be a function of the moving average of the gas-volumetric-fraction of the mixture and the total flow rate. In another aspect, the ultrasound transmitter/receivers are capable of detecting one or more ultrasonic flashes, ultrasonic flashes can then be used to determine the percentages of the two liquid phases in the mixture based on the arrival time of the ultrasonic flashes. In another aspect, the ultrasound transmitter/receivers are paired dual frequency (high and low) ultrasound transmitters/receivers. In another aspect, the ultrasound transmitter/receivers sample in the same direction and are positioned at a known distance and are used to determine flow velocity using signal cross-correlation. In another aspect, the device is defined further as comprising a Venturi tube and the computer calculates a total mass flow using the Venturi tube with real-time correction for mixture density provided by the GVF and a water cut measured by the meter.

In another aspect, the device is defined further as comprising a positive displacement flowmeter and the computer calculates a total mass flow using the positive displacement flowmeter with real-time correction for mixture density provided by the GVF and a water cut measured by the meter, to measure the total mass flow. In another aspect, the multiphase fluid mixture may comprise a gas phase; two or more liquids, wherein at least one of the liquid is a non-water liquid; or a gas and two liquids, wherein at least one of the liquid is a non-water liquid. In another aspect, the determination of the fractions of the multiphase fluid mixture is based on a detection of at least one characteristic of the detected ultrasonic wave in the multiphase fluid mixture. In another aspect, the device is capable of measuring at least one of a high, medium, or a low gas volumetric fraction (GVF) in the multiphase fluid mixture.

In another embodiment, the present invention includes a method for determining the flow of one or more phases of a multiphase fluid mixture comprising: positioning about a tube, a pipe, a main body or any combinations thereof comprising an interior and an exterior, a first ultrasound field detector ring comprising: two or more pairs of transversal paired dual frequency ultrasound transmitter/receivers that are on the same normal plane and are positioned in a transversal direction to a flow of the multiphase fluid mixture, wherein the sampled volume covers a part of or the entire cross-section of the interior of the tube, pipe, main body or any combinations thereof; wherein the transmitter/receivers are connected to a computer connected to the ultrasound transmitter/receivers; and calculating the one or more phases of a multiphase fluid mixture by measuring the ultrasound signal. In one aspect, the device further comprises one or more ultrasound field detector rings adjacent to the first ultrasound field detector ring, each of the one or more ultrasound field detectors positioned in a transversal direction to a flow of the multiphase fluid mixture. In another aspect, the device further comprises one or more ultrasound field detector rings adjacent to the first revolving ultrasound field detector ring are placed on one or more parallel planes. In another aspect, the device further comprises one or all of a pressure sensor to sense a fluid pressure of the multiphase fluid mixture, a temperature sensor to sense a fluid temperature of the multiphase fluid mixture, a Venturi flow meter for a real-time determination of the multiphase fluid mixture, and a computer to determine a gas fraction, a water fraction, and a non-water fluid fraction of the multiphase fluid mixture, based on the sensed fluid pressure, the sensed fluid temperature, and at least one characteristic of the detected ultrasonic wave in the multiphase fluid. In another aspect, the ultrasound transmitter/receivers are in contact with the multiphase fluid. In another aspect, the ultrasound transmitter/receivers are capable of at least one of: scanning at the same time, scanning in series, scanning in parallel, scanning in pulses, or scanning with one pair acting as a transmitter and the second pair acting as a receiver.

In another aspect, the method further comprises the step of estimating a Gas-Volumetric-Fraction (GVF) using the moving average of an amplitude of all signal(s) received by the ultrasound transmitter/receivers in a scan configuration after ultrasound propagation through the multiphase fluid mixture. In another aspect, the method further comprises the step of estimating a GVF using at least one characteristic of one or more of a signal(s) received for a scan configuration after propagation through the mixture at the ultrasound transmitter/receivers. In another aspect, the method further comprises the step of detecting one or more ultrasonic flashes that are transient in time and have at least one of a larger amplitude or different frequency spectra from that transmitted. In another aspect, the method further comprises the step of detecting one or more ultrasonic flashes that are transient in time and have at least one of larger amplitude and different frequency spectra from that transmitted, wherein the ultrasound flashes are calculated using a Fourier transform of the signal (spectral analysis). In another aspect, the method further comprises the step of detecting one or more ultrasonic flashes, wherein the detection threshold for flashes can be constant or can be a function of the moving average of the gas-volumetric-fraction of the mixture and the total flow rate. In another aspect, the method further comprises the step of detecting one or more ultrasonic flashes, ultrasonic flashes can then be used to determine the percentages of the two liquid phases in the mixture based on the arrival time of the ultrasonic flashes. In another aspect, the method further comprises the step of pairing dual frequency (high and low) ultrasound transmitters/receivers. In another aspect, the method further comprises the step of calculating total mass flow using a Venturi tube with real-time correction for mixture density provided by the GVF and a water cut measured by the meter. In another aspect, the method further comprises the step of calculating total mass flow using a positive displacement flowmeter with real-time correction for mixture density provided by the GVF and a water cut measured by the meter. In another aspect, the method further comprises the multiphase fluid mixture may comprise a gas phase; two or more liquids, wherein at least one of the liquid is a non-water liquid; or a gas and two liquids, wherein at least one of the liquid is a non-water liquid. In another aspect, the method further comprises the step of determining the fractions of the multiphase fluid mixture is based on a detection of at least one characteristic of the detected ultrasonic wave in the multiphase fluid mixture. In another aspect, the method further comprises the step of measuring a high medium or low gas volumetric fraction (GVF) in the multiphase fluid mixture.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Revolving US Field Multiphase Flowmeter.

Figure 1A:
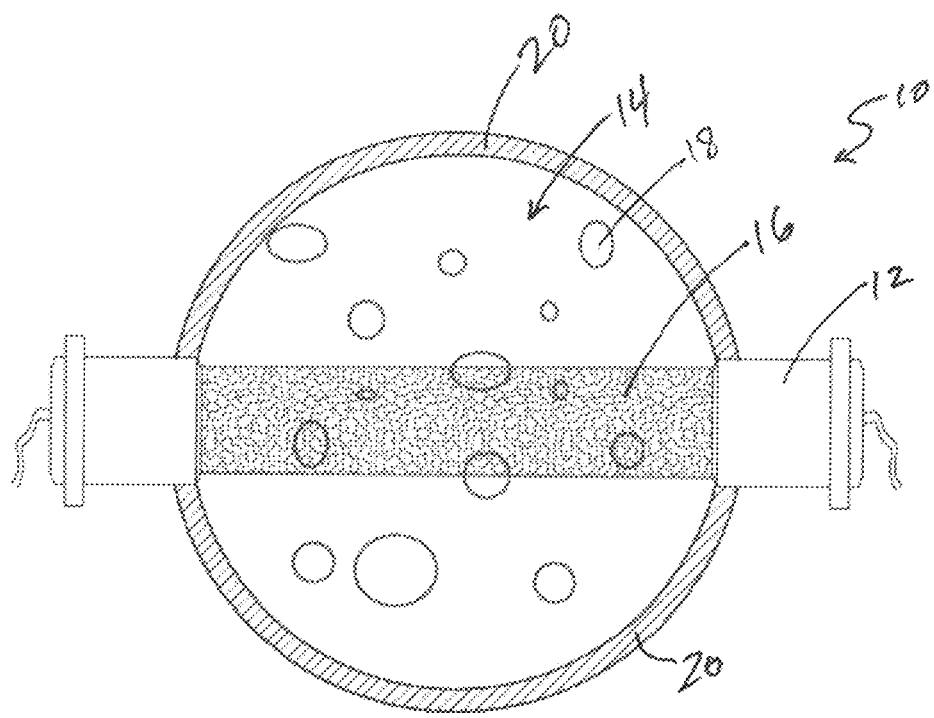
FIGS. 1A, 1B and 1C show three configurations of a multiphase fluid measuring device in which the total sampled volume for several transducer.
Figure 1B:
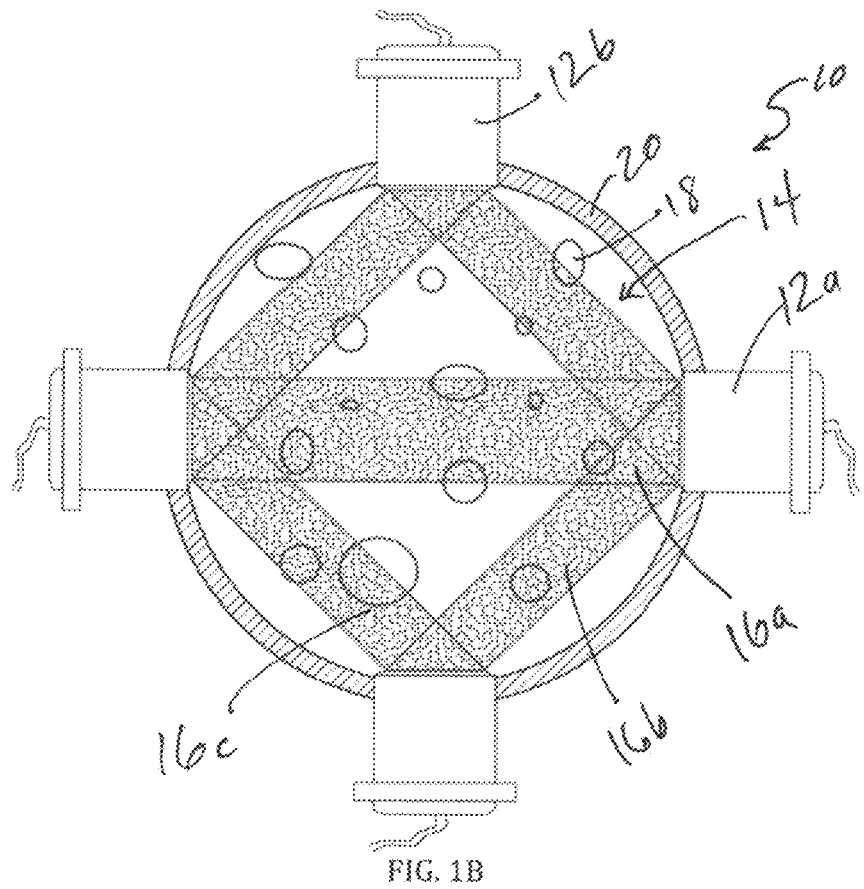
Figure 1C:
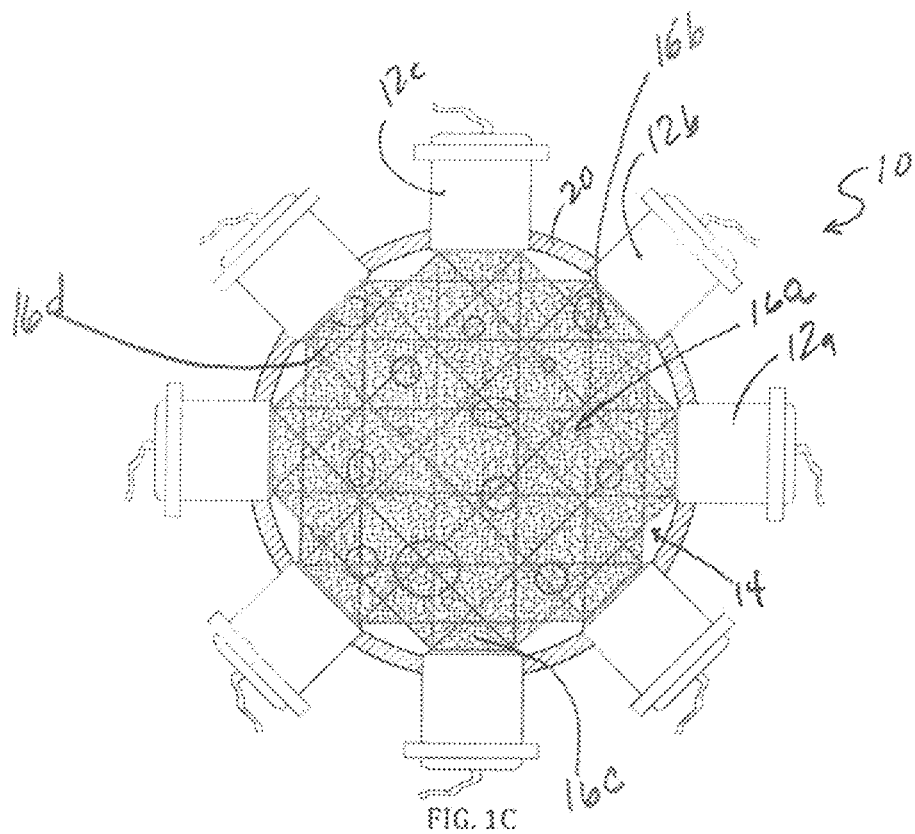

Method. The present invention provides a novel method to measure more accurately the liquid fractions in a three phase mixture in the presence of higher gas fractions than traditional ultrasound based multiphase flowmeters, by maximizing the sampled volume placing a number of transducers around the flow volume. FIGS. 1A to 1C show a comparison of the sampled volume for several transducer configurations.

Briefly, a multiphase flowmeter 10 is depicted with the transducers 12. The transducers 12 can also be described as an ultrasound transmitter-received pair or transversal paired dual frequency ultrasound transmitter/receivers; however, the skilled artisan will recognize that which of the halves of the transmitter-received pair can be a transmitter or receiver, i.e., a transceiver or transducer. The transducers 12 are positioned in a plane normal to the flow direction such that the sampled volume 14 covers a part of or the whole cross-section 16 of the flow volume, which are shown in contact with the sampled volume 14 traversing the pipe 20. The sampled volume 14 is shown with bubbles 18 and may also be further divided into oil and aqueous portions. FIGS. 1A to 1C show three configurations with a different number of transducers 12 placed on the perimeter of a section of the pipe 20. In the embodiment in FIG. 1B, the increased coverage of the various cross-sections 16a-c are depicted showing the capability of the transducers 12a, 12b to not only measure a signal from the other half of that specific transducer, but to pick up the partial cross-section from the perpendicular transducer. Thus, as shown in FIG. 1C, three transducers 12a-d are depicted that measure the bulk of the sampled volume 14 via cross-section 16a-d. The sampled volume, shown with pattern, increases as the number of transducers is increased.

Figure 2:
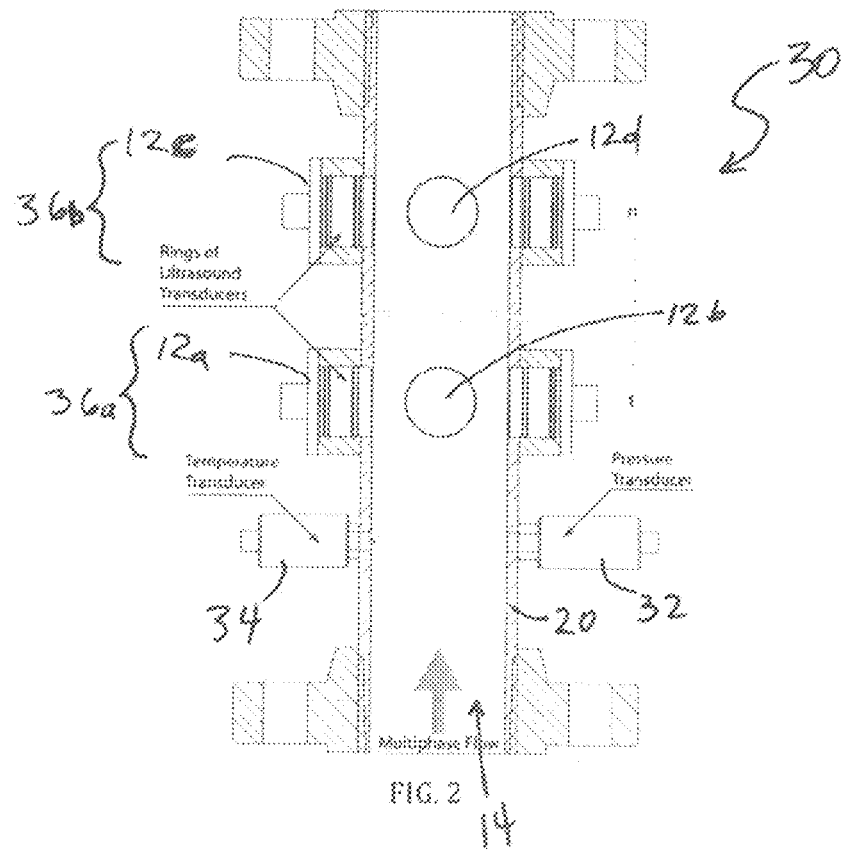
FIG. 2 shows a configuration in which rings of ultrasound transducers are placed along the longitudinal direction of the flowmeter.

FIG. 2 shows a side, cross-section view of the multiphase flow meter 30 present invention in the context of a pipe 20. A multiphase flow meter 30 is depicted with a pressure transducer 32 and temperature transducer 34 depicted in one portion of the pipe 20, adjacent first transducer ring 36a, which includes perpendicular transducers 12a,b. A second ring 36b is depicted downstream from the first transducer ring 36a, as the flow is depicted as traversing the pipe 20 and contacting the first transducer ring 36a and the second transducer ring 36b downstream. Multiple rings of ultrasound transducers 36a-n (depicted as 1 . . . n) can be placed along the longitudinal direction of the flowmeter on the pipe 20. Thus, several "rings" of transducers can be positioned in parallel planes along the longitudinal direction of the pipe 20 (flowmeters) to increase the sampled volume and to improve the precision and accuracy of the measurement, as seen in FIG. 2.

A scan configuration can be defined by assigning one or more transducers as emitter(s), while any number of them, which may include the emitters themselves, will act as receivers. A wide range of scan sequences can be generated by using any desired set of successive scan configuration at specific time intervals.

Figure 3:
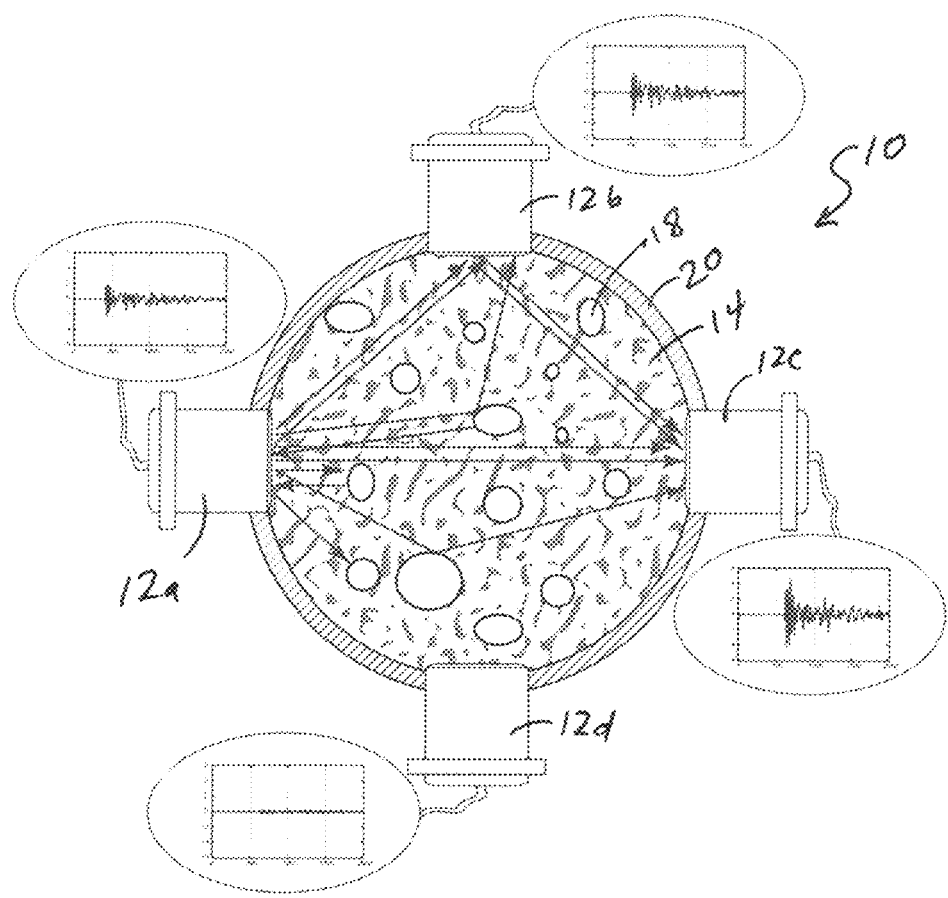
FIG. 3 shows one example of a scan configuration with one transducer acting as emitter, and the others acting as receivers. The emitter itself switches in receiving mode after the initial ultrasound pulse.
Figure 4A:
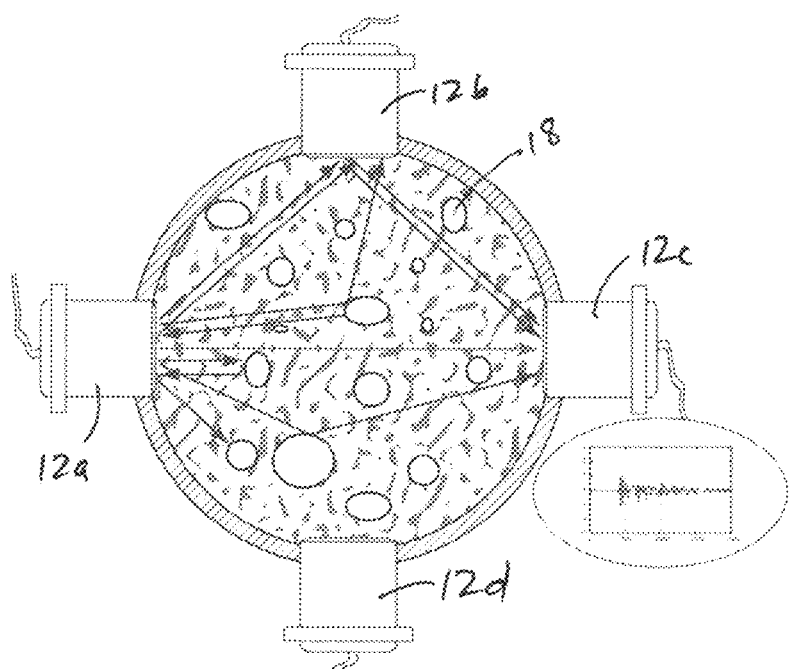
FIGS. 4A to 4D show two typical signal paths through multiphase mixture (FIG. 4A) and received signal at the transducer (FIG. 4C), "Flash" signal path (FIG. 4B), and corresponding received signal at the transducer (FIG. 4D).
Figure 4B:
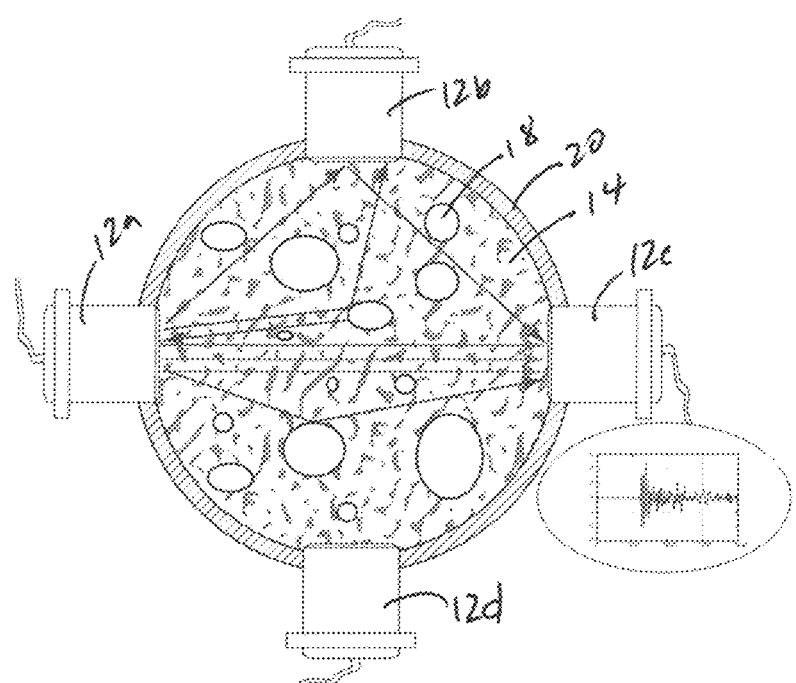

FIG. 3 shows one example of a scan configuration with one transducer 12a acting as an emitter (see arrows), and the others acting as receivers 12b-d. The signal received at the various transducers 12a-d are shown as graphs in which the signal received is depicted with the various reflections measured as shown in the graphs. The emitter itself switches in receiving mode after the initial ultrasound pulse. Thus, the present invention can be used to calculate one or more of the following: (1) Gas-Volumetric-Fraction (GVF) is estimated using the moving average of the amplitude of all signal(s) received for a scan configuration after propagation through the mixture; (2) GVF can be estimated using at least one characteristic of one or more of the signal(s) received for a scan configuration after propagation through the mixture; and (3) liquid fraction. In a typical flow configuration the signal received across the sampled volume consists of a combination of reflected and directly transmitted ultrasound waves as seen in FIG. 4A. The corresponding transducer signal has relatively low amplitude and can exhibit delayed arrival time due to longer propagation path (tortuosity). To accurately determine the liquid fraction it is necessary to identify signals that for the most part travelled through low gas paths in the mixture (FIG. 4B). These signals, called "ultrasonic flashes", will be transient in time and will have in general larger amplitude and different frequency spectra. The flashes are detected using a specialized algorithm that compares the characteristics of the typical signal to the signal amplitude and/or the spectral characteristics measured in the Fourier transform of the signal (spectral analysis). The detection threshold for flashes can be constant or can be a function of the moving average of the gas-volumetric-fraction of the mixture and the total flow rate.

Figure 4C:
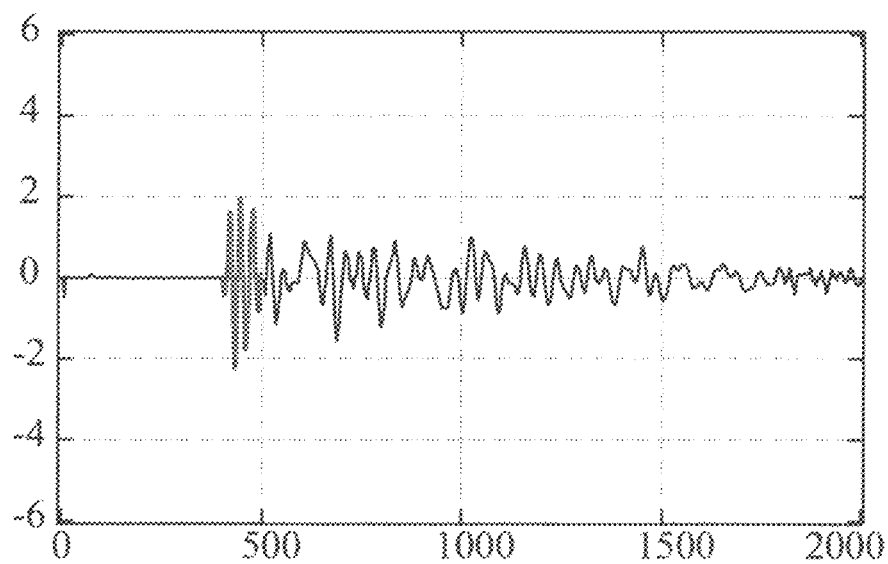
Figure 4D:
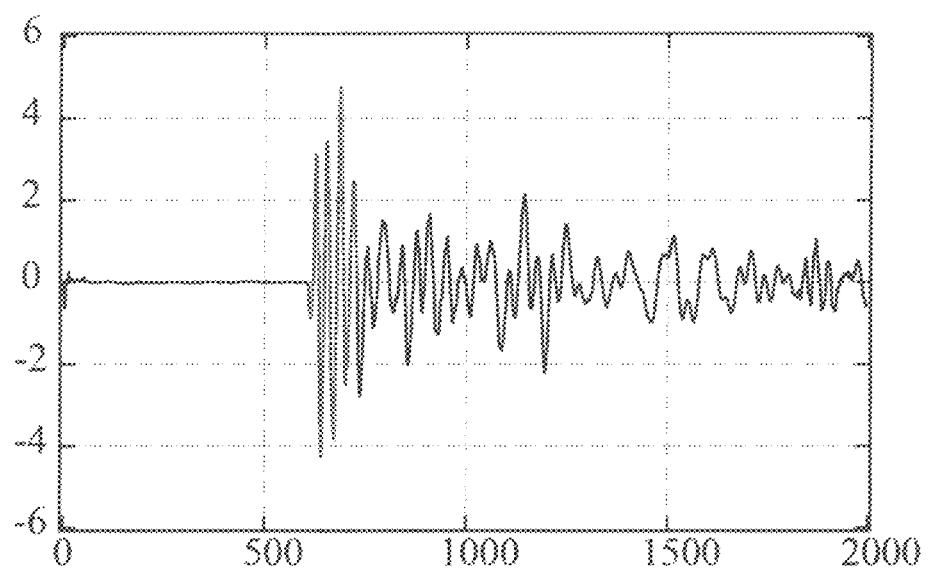

Thus, using the present invention, the arrival time of the ultrasonic flashes can then be used to determine the percentages of two liquid phases in the multiphase mixture. FIGS. 4A to 4D show two examples of typical signal paths through multiphase mixture. FIGS. 4A and 4C show the typical signal path (4A) and the received signal at the transducer (4C). FIGS. 4B and 4D show a "flash" signal path (4B) and corresponding received signal at the transducer (4D), in which the signal is shown in the graph and in which little to no deflection from gas or the minor fraction (oil or aqueous, depending on what is the majority of the flow).

Thus, the apparatus and method of the present invention evaluates the phase fractions (gas, oil, water). To determine the flow rates of each individual phase, a total mass or volumetric flow device is used.

In one embodiment of the apparatus of the present invention there can be an even (or an odd number other than 1) of radially symmetric transducers. For example, paired dual frequency (high and low) ultrasound transmitters/receivers in a transversal direction to the flow can also be used. These transducers can be arranged in the form of diametrically opposed pairs. In other embodiments, the transducers pairs can have a radial angled placement along the longitudinal direction of the flow for thorough sampling of the mixture. Thus, using the present invention a more complete or total flow measurement can be obtained, including: (1) ultrasound transducer pairs sampling in the same direction, positioned at a known distance in the longitudinal direction of flow are used to determine flow velocity using signal cross-correlation; (2) Venturi tube with real-time correction for mixture density provided by the GVF and water cut measured by the fraction meter; and (3) positive displacement flowmeter.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A device for determining the flow of one or more phases of a multiphase fluid mixture comprising:
 a tube, a pipe, a main body or any combinations thereof comprising an interior and an exterior, wherein the interior receives a multiphase fluid mixture for the determination of the fractions in the multiphase;
 a first ultrasound field detector ring comprising: two or more pairs of transversal paired dual frequency ultrasound transmitter/receivers are on the same normal plane and are positioned in a transversal direction to a flow of the multiphase fluid mixture on the exterior of the tube, pipe, or main body, wherein the sampled volume covers a part of or the whole cross-section of the flow volume; and a computer connected to the ultrasound transmitter/receivers that determines the one or more phases of a multiphase fluid mixture.

2. The device of claim 1, wherein the device further comprises one or more ultrasound field detector rings adjacent to the first ultrasound field detector ring, each of the one or more ultrasound field detectors positioned in a transversal direction to a flow of the multiphase fluid mixture.

3. The device of claim 1, wherein the device further comprises one or more ultrasound field detector rings adjacent to the first ultrasound field detector ring are placed on one or more parallel planes.

4. The device of claim 1, wherein the device further comprises a pressure sensor to sense a fluid pressure of the multiphase fluid mixture, a temperature sensor to sense a fluid temperature of the multiphase fluid mixture, a Venturi flow meter for a real-time determination of the multiphase fluid mixture, and a computer to determine a gas fraction, a water fraction, and a non-water fluid fraction of the multiphase fluid mixture, based on the sensed fluid pressure, the sensed fluid temperature, and at least one characteristic of the detected ultrasonic wave in the multiphase fluid.

5. The device of claim 1, wherein the ultrasound transmitter/receivers are in contact with the multiphase fluid.

6. The device of claim 1, wherein the ultrasound transmitter/receivers are capable of at least one of: scanning at the same time, scanning in series, scanning in parallel, scanning in pulses, or scanning with one pair acting as a transmitter and the second pair acting as a receiver.

7. The device of claim 1, wherein a Gas-Volumetric-Fraction (GVF) is estimated using a moving average of an amplitude of all signal(s) received by the ultrasound transmitter/receivers in a scan configuration after ultrasound propagation through the multiphase fluid mixture.

8. The device of claim 1, wherein a GVF is estimated using at least one characteristic of one or more of a signal(s) received for a scan configuration after propagation through the mixture at the ultrasound transmitter/receivers.

9. The device of claim 1, wherein the ultrasound transmitter/receivers are capable of detecting one or more ultrasonic flashes that are transient in time and have at least one of a larger amplitude or a different frequency spectra from that transmitted.

10. The device of claim 1, wherein the ultrasound transmitter/receivers are capable of detecting one or more ultrasonic flashes that are transient in time and have at least one or a larger amplitude or different frequency spectra from that transmitted, wherein the ultrasound flashes are calculated using a Fourier transform of the signal (spectral analysis).

11. The device of claim 1, wherein the ultrasound transmitter/receivers are capable of detecting one or more ultrasonic flashes, wherein the detection threshold for flashes can be constant or can be a function of the moving average of the gas-volumetric-fraction of the mixture and the total flow rate.

12. The device of claim 1, wherein the ultrasound transmitter/receivers are capable of detecting one or more ultrasonic flashes, ultrasonic flashes can then be used to determine the percentages of the two liquid phases in the mixture based on the arrival time of the ultrasonic flashes.

13. The device of claim 1, wherein the ultrasound transmitter/receivers are paired dual frequency (high and low) or multi frequency ultrasound transmitters/receivers.

14. The device of claim 1, wherein the ultrasound transmitter/receivers sample in the same direction and are positioned at a known distance and are used to determine flow velocity using signal cross-correlation.

15. The device of claim 1, wherein the device is defined further as comprising a Venturi tube and the computer calculates a total mass flow using the Venturi tube with real-time correction for mixture density provided by the GVF and a water cut measured by the meter.

16. The device of claim 1, wherein the device is defined further as comprising a positive displacement flowmeter and the computer calculates a total mass flow using the positive displacement flowmeter with real-time correction for mixture density provided by the GVF and a water cut measured by the meter, to measure the total mass flow.

17. The device of claim 1, wherein the multiphase fluid mixture may comprise a gas phase; two or more liquids, wherein at least one of the liquid is a non-water liquid; or a gas and two liquids, wherein at least one of the liquid is a non-water liquid.

18. The device of claim 1, wherein the determination of the fractions of the multiphase fluid mixture is based on a detection of at least one characteristic of the detected ultrasonic wave in the multiphase fluid mixture.

19. The device of claim 1, wherein the device is capable of measuring at least one of a high, medium, or a low gas volumetric fraction (GVF) in the multiphase fluid mixture.

20. A method for determining the flow of one or more phases of a multiphase fluid mixture comprising:

positioning about a tube, a pipe, a main body or any combinations thereof comprising an interior and an exterior, a first ultrasound field detector ring comprising:

two or more pairs of transversal paired dual frequency ultrasound transmitter/receivers that are on the same normal plane and are positioned in a transversal direction to a flow of the multiphase fluid mixture, wherein the sampled volume covers a part of or the entire cross-section of the interior of the tube, pipe, main body or any combinations thereof; wherein the transmitter/receivers are connected to a computer connected to the ultrasound transmitter/receivers; and calculating the one or more phases of a multiphase fluid mixture by measuring the ultrasound signal.

21. The method of claim 20, wherein the device further comprises one or more ultrasound field detector rings adjacent to the first ultrasound field detector ring, each of the one or more ultrasound field detectors positioned in a transversal direction to a flow of the multiphase fluid mixture.

22. The method of claim 20, wherein the device further comprises one or more ultrasound field detector rings adjacent to the first revolving ultrasound field detector ring are placed on one or more parallel planes.

23. The method of claim 20, wherein the device further comprises a pressure sensor to sense a fluid pressure of the multiphase fluid mixture, a temperature sensor to sense a fluid temperature of the multiphase fluid mixture, a Venturi flow meter for a real-time determination of the multiphase fluid mixture, and a computer to determine a gas fraction, a water fraction, and a non-water fluid fraction of the multiphase fluid mixture, based on the sensed fluid pressure, the sensed fluid temperature, and at least one characteristic of the detected ultrasonic wave in the multiphase fluid.

24. The method of claim 20, wherein the ultrasound transmitter/receivers are in contact with the multiphase fluid.

25. The method of claim 20, wherein the ultrasound transmitter/receivers are capable of at least one of: scanning at the same time, scanning in series, scanning in parallel, scanning in pulses, or scanning with one pair acting as a transmitter and the second pair acting as a receiver.

26. The method of claim 20, further comprising the step of estimating a Gas-Volumetric-Fraction (GVF) using the moving average of an amplitude of all signal(s) received by the ultrasound transmitter/receivers in a scan configuration after ultrasound propagation through the multiphase fluid mixture.

27. The method of claim 20, further comprising the step of estimating a GVF using at least one characteristic of one or more of a signal(s) received for a scan configuration after propagation through the mixture at the ultrasound transmitter/receivers.

28. The method of claim 20, further comprising the step of detecting one or more ultrasonic flashes that are transient in time and have at least one of a larger amplitude or different frequency spectra from that transmitted.

29. The method of claim 20, further comprising the step of detecting one or more ultrasonic flashes that are transient in time and have at least one of larger amplitude and different frequency spectra from that transmitted, wherein the ultrasound flashes are calculated using a Fourier transform of the signal (spectral analysis).

30. The method of claim 20, further comprising the step of detecting one or more ultrasonic flashes, wherein the detection threshold for flashes can be constant or can be a function of the moving average of the gas-volumetric-fraction of the mixture and the total flow rate.

31. The method of claim 20, further comprising the step of detecting one or more ultrasonic flashes, ultrasonic flashes can then be used to determine the percentages of the two liquid phases in the mixture based on the arrival time of the ultrasonic flashes.

32. The method of claim 20, further comprising the step of pairing dual frequency (high and low) ultrasound transmitters/receivers.

33. The method of claim 20, further comprising the step of calculating total mass flow using a Venturi tube with real-time correction for mixture density provided by the GVF and a water cut measured by the meter.

34. The method of claim 20, further comprising the step of calculating total mass flow using a positive displacement flowmeter with real-time correction for mixture density provided by the GVF and a water cut measured by the meter.

35. The method of claim 20, wherein the multiphase fluid mixture may comprise a gas phase; two or more liquids, wherein at least one of the liquid is a non-water liquid; or a gas and two liquids, wherein at least one of the liquid is a non-water liquid.

36. The method of claim 20, further comprising the step of determining the fractions of the multiphase fluid mixture is based on a detection of at least one characteristic of the detected ultrasonic wave in the multiphase fluid mixture.

37. The method of claim 20, further comprising the step of measuring a high medium or low gas volumetric fraction (GVF) in the multiphase fluid mixture.

* * * * *